United States Patent [19]
Kocinski

[11] Patent Number: 5,170,782
[45] Date of Patent: Dec. 15, 1992

[54] MEDICAMENT NEBULIZER WITH IMPROVED AEROSOL CHAMBER

[75] Inventor: Richard J. Kocinski, Somerset, Pa.

[73] Assignee: DeVilbiss Health Care, Inc., Somerset, Pa.

[21] Appl. No.: 758,742

[22] Filed: Sep. 12, 1991

[51] Int. Cl.$^5$ ............................................. A61M 11/00
[52] U.S. Cl. ........................... 128/200.16; 128/200.18; 128/203.12; 239/338; 261/78.1; 261/DIG. 65; 261/DIG. 48
[58] Field of Search ....................... 128/200.11, 200.12, 128/200.13, 200.14, 200.16, 200.18, 200.19, 200.21, 203.12, 203.24, 203.25; 239/102.2, 337, 338, 339, 418, 426; 261/78.1, 115, 116, DIG. 65, DIG. 48

[56] References Cited

U.S. PATENT DOCUMENTS

| | | | |
|---|---|---|---|
| 1,410,556 | 3/1922 | Dorment | 128/203.24 |
| 1,839,193 | 1/1932 | Blanchard | 128/200.18 X |
| 2,546,214 | 3/1951 | Curry | 128/200.18 X |
| 3,561,444 | 2/1971 | Boucher | 261/DIG. 65 X |
| 3,658,059 | 4/1972 | Steil | 128/200.21 |
| 3,861,386 | 1/1975 | Harris et al. | 128/200.16 |
| 3,864,326 | 2/1975 | Babington | 128/200.18 X |
| 3,900,138 | 8/1975 | Phillips | 128/200.14 X |
| 4,007,238 | 2/1977 | Glenn | 128/200.18 X |
| 4,094,317 | 6/1978 | Wasnich | 128/200.16 |
| 4,113,809 | 9/1978 | Abair et al. | 128/200.16 X |
| 4,116,387 | 9/1978 | Kremer et al. | 128/200.18 X |
| 4,251,033 | 2/1981 | Rich et al. | 128/200.18 X |
| 4,429,835 | 2/1984 | Brugger et al. | 128/200.18 X |
| 4,976,259 | 12/1990 | Ifigson et al. | |

OTHER PUBLICATIONS

Porta-Sonic Ultrasonic Nebulizer Patient Guide-1989 brochure-DeVilbiss Health Care, Inc.
Cyclones, Centrifuges and Diffusion Sampler, D. A. Lundgren, University of Florida.
The Spiral Drug-Inhaler—undated brochure—Medisonic U.S.A. Inc.

Primary Examiner—V. Millin
Assistant Examiner—Sebastiano Passaniti
Attorney, Agent, or Firm—MacMillan, Sobanski & Todd

[57] ABSTRACT

An improved aerosol chamber for an ultrasonic nebulizer which prevents relatively large medicament droplets from being inhaled by a patient. The chamber has a housing formed from a polycarbonate resin and is generally cylindrically shaped with a spherical top surface. The chamber includes an air inlet formed in the top surface and an aerosol outlet formed in a side surface. A centrally located mist tube extends coaxial from the air intake downwardly past the aerosol outlet. A longitudinally extending slot is formed in the mist tube facing the side surface of the housing diametrically opposite the outlet. The slot extends from a lower edge of the tube upwardly toward the air intake. A geyser baffle is disposed at an angle within the mist tube above the slot to deflect larger droplets away from the slot. The baffle includes an upper edge spaced from an adjacent inner surface of the mist tube to define a relatively small gap to allow inlet air to flow through the mist tube. The air flow entrains nebulized medicament droplets, flows through the slot and through an annular space between the mist tube and the housing to the outlet. The annular space creates a cyclone effect which causes larger droplets to condense on the interior walls of the housing.

7 Claims, 2 Drawing Sheets

MEDICAMENT NEBULIZER WITH IMPROVED AEROSOL CHAMBER

TECHNICAL FIELD

The invention relates in general to ultrasonic nebulizers for administering a medicamentous aerosol to a patient's respiratory system and in particular to an improved aerosol dome chamber for use with such an ultrasonic nebulizer which prevents relatively large aerosol particles from being inhaled by the patient.

BACKGROUND ART

Medical nebulizers are used to deliver a prescribed medication, i.e., a medicated inhalant, as an aerosol to the lungs of a patient for direct absorption by the affected area. The nebulizer produces an aerosol either by forcing the liquid medicament through a nozzle, or by air atomization or by ultrasonic atomization. All three types of nebulizers can provide a convenient and efficient method for administering drugs to patients suffering from respiratory problems, such as, chronic pulmonary disease, asthma, and allergies. While all three types of nebulizers transform a liquid medicament into a mist, the ultrasonic nebulizers can produce the finest mist and are quieter than air atomizers which require a compressor.

The ultrasonic nebulizer can operate as a "patient demand" system. In simplest terms, a patient demand system pulls the medicament aerosol from a nebulizing chamber and delivers the aerosol to the patient only during inhalation. When the patient exhales or takes a break from treatment, the medication condenses in the chamber where it is re-nebulized until inhaled by the patient. The ultrasonic nebulizer operated as a patient demand system that is economical and efficient since the medication is delivered only to the affected area and only when needed. This minimizes the drug losses to the atmosphere and by delivery to unaffected areas and therefore eliminates the need for larger drug doses in order to compensate for loses. In addition, since the drug is more precisely delivered to the affected areas, the chance of an adverse drug reaction by the patient is reduced.

The size of the aerosol droplets is critical in patient treatment since finer droplets more deeply penetrate the affected area as well as increase the ability of the lungs to absorb such droplets. However, there has been no efficient device for ensuring that the size of the medicated aerosol particles which are delivered to the patient are relatively fine. In an ultrasonic nebulizer, a geyser containing a range of droplet sizes is formed. It is desirable to provide an ultrasonic nebulizer wherein only relatively fine droplets of a medicated aerosol are capable of being inhaled by a patient.

DISCLOSURE OF THE INVENTION

The invention is directed to an improved aerosol chamber for use with an ultrasonic nebulizer which prevents relatively large atomized medicament droplets from being inhaled by a patient. The chamber has a housing which is attached to an ultrasonic nebulizer base above a liquid reservoir. An ultrasonic transducer in the base causes a geyser of liquid droplets to erupt from the liquid surface in the reservoir. The chamber housing is generally cylindrical in shape, has a spherical top, surface, and preferably is formed from a polycarbonate resin. The chamber housing has an air inlet formed in the top surface and has an aerosol outlet formed in a side surface. A centrally located mist tube depends from the top surface into the dome. The mist tube extends coaxial with the air inlet downwardly past the aerosol outlet. The mist tube is provided with a vertically extending slot or passage facing away from the aerosol outlet. The slot extends from a lower edge of the tube upwardly toward the air inlet.

A geyser baffle is secured within the mist tube. The geyser baffle begins immediately above the slot and extends upwardly at an angle to the axis of the mist tube. The geyser baffle closes the mist tube except for an upper edge spaced from an adjacent inner surface of the mist tube to define a relatively small gap. This gap is the only air passage in the mist tube between the air inlet and the slot. The geyser baffle is angled to direct larger droplets away from the mist tube slot. The mist tube and the chamber housing create a cyclone effect which is effective to cause larger droplets to condense and return to the fluid reservoir before they can be delivered to the patient.

Accordingly, it is an object of the invention to provide an improved aerosol chamber for an ultrasonic nebulizer which reduces the possibility of relatively large medicament droplets from being delivered to a patient.

Other objects and advantages of the invention will become apparent to those skilled in the art from the following detailed description and the accompanying drawings.

BEST MODE FOR CARRYING OUT THE INVENTION

Figure 1:
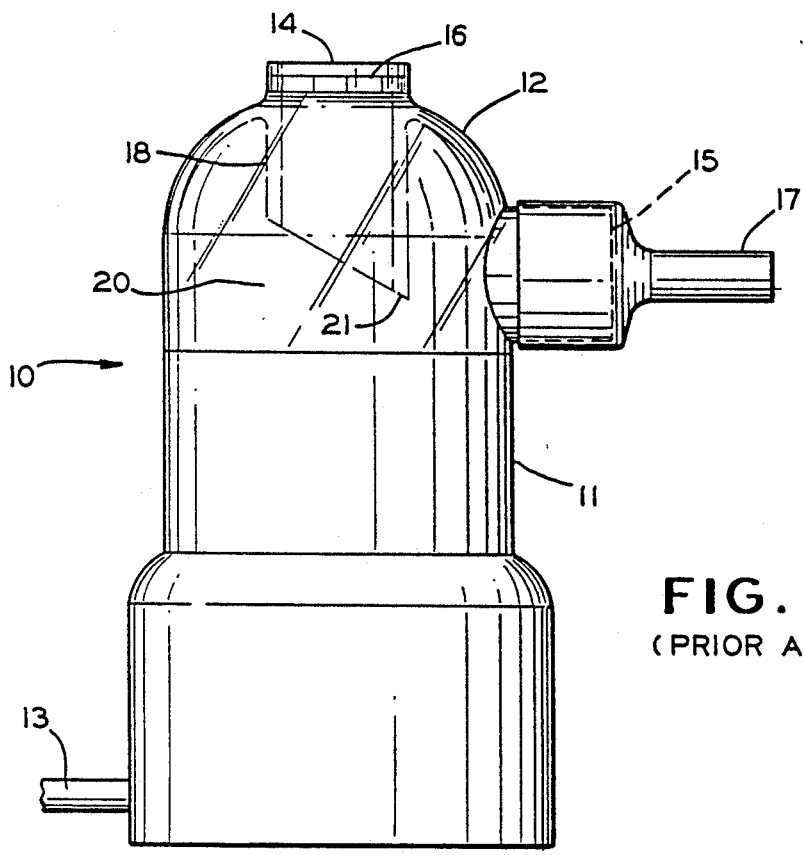
FIG. 1 is a side elevational view of a prior art ultrasonic nebulizer.

Referring to the drawings, FIG. 1 illustrates a prior art ultrasonic nebulizer 10 including a nebulizer base 11 and an aerosol chamber or dome 12. A cord 13 (shown in fragmentary) is connected from a transducer (not shown) in the base 11 to an external high frequency power source (not shown). The aerosol dome 12 is provided with an air intake 14 and an aerosol outlet 15. The inlet 14 is centrally located on the top of the dome 12. A check valve 16 in the inlet 14 allows air to be drawn only through the inlet 14 into the dome 12. The prior art nebulizer 10 further includes a replaceable mouthpiece 17 attached to the aerosol outlet 15.

A tube 18 is secured in the dome 12 coaxial with the inlet 14 and extends downwardly into an aerosol chamber 20 formed by the interior of the dome 12. The tube 18 has a beveled lower end 21 which is angled away from the outlet 15. In operation, a geyser of nebulized medicament is propelled upwardly into the chamber 20 from the center of the base 11. A patient inserts the mouthpiece 17 in his or her mouth and inhales, drawing air in through the inlet check valve 16, mixing the air with the atomized liquid in the chamber 20 and then drawing the air/atomized medicament through the outlet 15 and the mouthpiece 17 to the affected area of the lungs. The tube 18 prevents air flow directly from the inlet 14 to the outlet 15 without picking up aerosol. The aerosol created in the prior art nebulizers has a range of droplet sizes. The prior art nebulizer design does not ensure that only relatively fine medicament droplets will be inhaled by a patient or that the maximum amount of the smallest droplets produced by the nebulizer are delivered.

Figure 2:
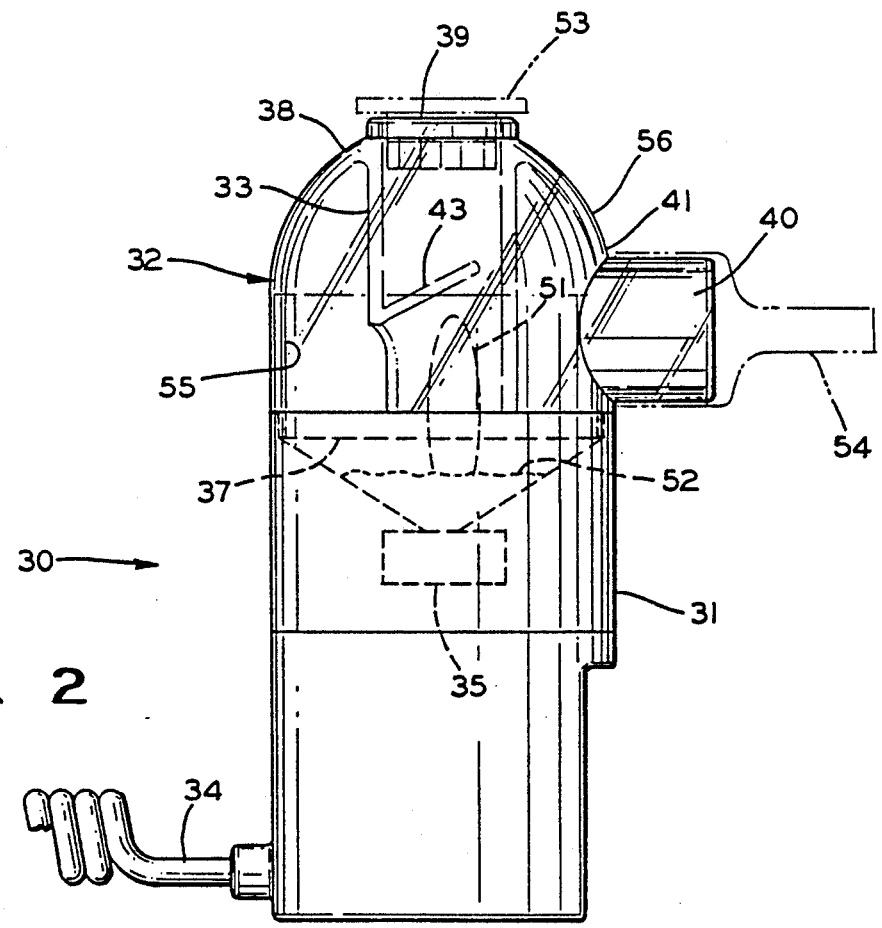
FIG. 2 is a side elevational view of an ultrasonic nebulizer including an improved aerosol chamber constructed in accordance with this invention.
Figure 3:
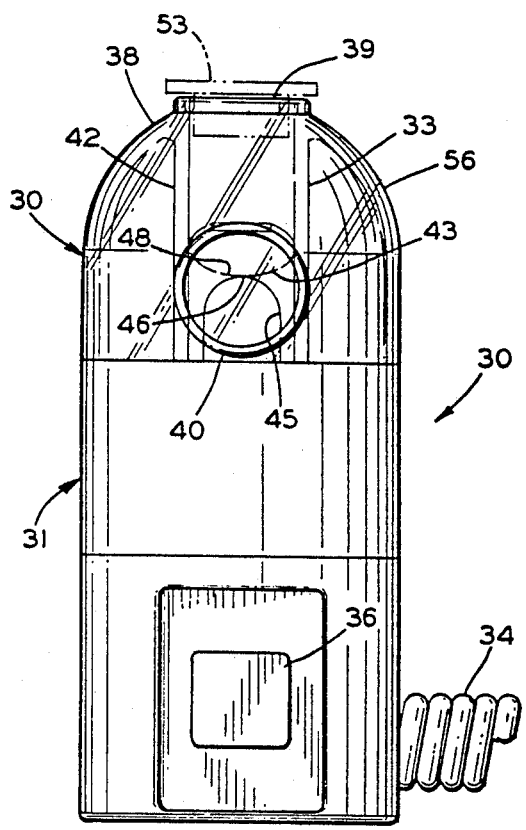
FIG. 3 is a front elevational view of the ultrasonic nebulizer illustrated in FIG. 2.

In accordance with the present invention, FIGS. 2-3 illustrate an ultrasonic nebulizer 30 including a nebulizer base 31 and an improved aerosol dome or chamber 32 consisting of a housing 56 containing a baffle assembly 33, constructed in accordance with the invention.

A coiled cord 34 (shown in fragmentary) is connected to the nebulizer 30 and connects a transducer 35 in the nebulizer 10 to a suitable high frequency power source (not shown). The aerosol chamber 32 is preferably constructed from a polycarbonate resin. The nebulizer base 31 and the cord 34 preferably are sealed to allow the nebulizer 30 to be submerged into solutions for cleaning. A membrane switch 36 is located on the front of the cup 31. The membrane switch 36 provides patient feedback to controlling electronics for the power source to turn on and off the transducer 35.

The chamber housing 56 is generally tubular and has a lower end 37 which is stepped for sliding onto the base 11 and has a spherical upper end 38. The upper end 38 is closed, except for an air inlet 39 which is centered above the transducer 35. An aerosol outlet 40 is located on a side 41 of the chamber 32. A removeable one-way check valve 53, shown in phantom in FIGS. 2 and 3, is pressed into the air inlet 36 to allow air to only be drawn into the chamber 32 during operation and to prevent aerosol from escaping through the inlet 36. A disposable mouthpiece 54, shown in phantom in FIG. 2, is attached to the outlet 40.

The baffle assembly 33 consists of a mist tube 42 and a geyser baffle 43. The mist tube 42 is generally cylindrical in shape and extends downwardly in the housing 56 coaxially with the air inlet 39. The mist tube 42 has a lower edge 44 and a longitudinally extending slot 45 which extends upwardly from the edge 44 to an upper end 46. The end 46 is semi-circular in shape.

Figure 4:
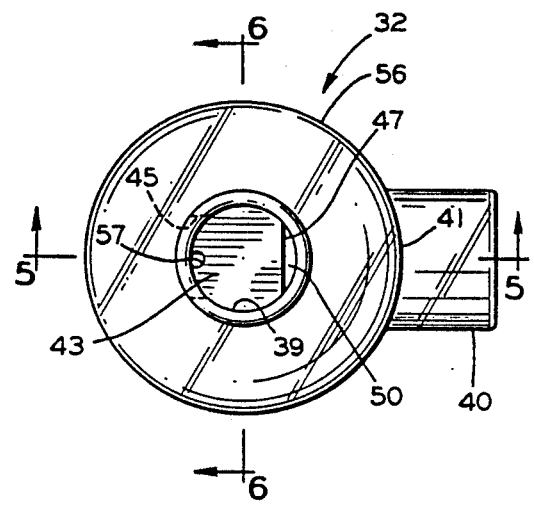
FIG. 4 is a top plan view of the aerosol chamber for the nebulizer illustrated in FIG. 2.
Figure 5:
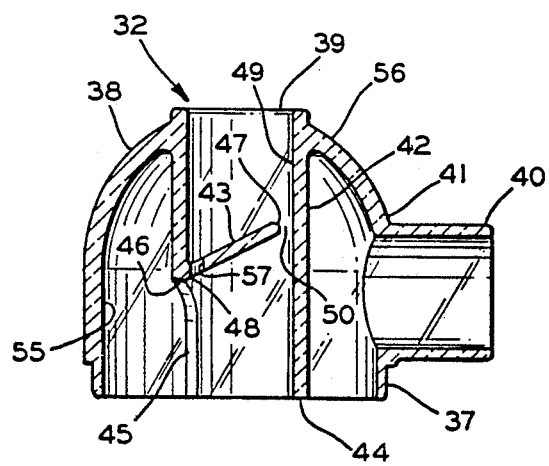
FIG. 5 is a cross-sectional view taken along line 5—5 of FIG. 4 and showing the details of aerosol chamber of the invention.
Figure 6:
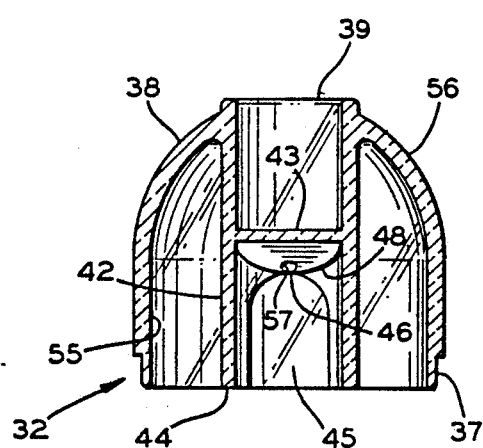
FIG. 6 is a cross-sectional view taken along line 6—6 of FIG. 4 and showing further details of the aerosol chamber of the invention.

The geyser baffle 43 has an upper flat free edge 47 (shown in FIG. 4) and has a lower edge 48 which is secured to the mist tube 42 (shown in FIG. 6). A small drain hole 57 extends through the lower edge 48. The baffle 43 is secured within the mist tube 42 to extend from adjacent the upper slot end 46 upwardly at an angle of approximately 30°, with its flat free edge 47 spaced from an inner wall 49 of the tube 42 to form a gap 50. The gap 50, best seen in FIGS. 4 and 5, defines the only passage for air flowing through the inlet 39.

The improved design of the aerosol chamber 32 and the geyser baffle assembly 33 reduces the possibility of relatively larger sized droplets of medicated aerosol from being ingested by a patient in the following manner. In operation, a geyser 51 of nebulized medication is produced above a volume of liquid 52 (FIG. 2) in the nebulizer base 31 and is propelled directly upwardly from the base 31 into the mist tube 42. The baffle 43 deflects droplets in the geyser 51 to prevent them from falling back down into the geyser 51, thus temporarily dampening the geyser 51. Any droplets which contact the geyser baffle 43 or the interior of the mist tube 42 condense and flow back to the volume of liquid 52 in the base 31.

The patient inserts the mouthpiece 54 into his or her mouth, forms a seal about the mouthpiece 54 with his or her lips, and inhales, taking slow, deep breaths. This causes the check valve 53 in the air intake 39 to open allowing air to descend in the mist tube 42 past the baffle 43 via the gap 50 and out the mist tube 42 through the slot 45. The inhaled air mixes with the nebulized medication which has been first reduced in size by the geyser baffle 43 to form a medicated aerosol. Since all of the air flow through the chamber 32 passes the geyser 51, the smallest droplets in the geyser 51 are readily entrained in the air flow to the patient. The medicated aerosol exits the tube 42 through the outlet port 45 and must then circle around through an annular space between the outside surface of the tube 42 and an interior wall 55 of the dome 32, exiting the chamber 32 via the outlet 40. This circling of the medicated aerosol within the chamber 32 creates a cyclone effect which tends to impact any larger droplets of medicated aerosol on the interior wall 55 of the chamber 32 where they are condensed and returned to the liquid 52 in the nebulizer base 31. The largest droplets tend to impact the dome wall 55 opposite the slot 45 and the smaller droplets impact the wall 55 further around the dome 32 from the slot 45. Only the smallest droplets remain entrained in the air at the outlet 40. This is due to the fact that as the aerosol travels along a curved path, the smaller droplets will follow the air stream while the larger droplets will follow a more straight path due to their inertia and will impact the wall 55. Thus, the cyclone effect created within the aerosol chamber 32 effectively reduces the possibility of any larger sized particles being inhaled by the patient.

Accordingly, the improved design of the present invention reduces the possibility of relatively larger sized droplets of medicated aerosol from being inhaled by the patient by initially deflecting these droplets against the geyser baffle 43 and the mist tube 42 and then further subjecting any remaining droplets to the cyclone effect created within the aerosol chamber 32. Furthermore, if an inexperienced patient does not take a slow deep breath but instead inhales suddenly, the cyclone effect will further increase because of the increased velocity. This ensures that any larger sized droplets will impact against and condense on the chamber wall 55 instead of being inhaled by the patient as may occur with the prior art nebulizer design discussed above.

Various modifications and changes may be made to the above described preferred embodiment of an improved aerosol chamber for a medicament nebulizer without departing from the spirit and the scope of the following claims.

I claim:

1. An improved aerosol chamber for use with an ultrasonic nebulizer base comprising a generally cylindrically shaped housing having a top surface containing an air inlet and a curved side wall containing an outlet, a mist tube having an axis and depending axially from said top surface to at least as far as a bottom of said outlet to form an annular space defining a curved flow path along said side wall between said mist tube and said housing, said mist tube surrounding said air inlet, means for mounting said housing on the nebulizer base whereby a geyser of nebulized medicament erupts from the base axially upwardly into said mist tube, said mist tube having a passage formed in a wall of said mist tube to face said curved housing side wall diametrically opposite said outlet whereby air flow from said air inlet to said outlet passes downwardly through said mist tube to entrain nebulized medicament droplets and then flows through said mist tube passage and along said curved path to said outlet.

2. An improved aerosol chamber for use with an ultrasonic nebulizer base, as set forth in claim 1, wherein said top housing surface is generally spherical.

3. An improved aerosol chamber for use with an ultrasonic nebulizer base, as set forth in claim 1, and further including a check valve mounted in said air inlet, said check valve preventing fluid flow from said mist tube through said air inlet while permitting air flow from said air inlet into said mist tube.

4. An improved aerosol chamber for use with an ultrasonic nebulizer base, as set forth in claim 1, wherein air flow and entrained droplets flow from said passage to said outlet along either of two curved paths extending along diametrically opposite portions of said side wall.

5. An improved aerosol chamber for use with an ultrasonic nebulizer base, as set forth in claim 1, and further including a baffle secured in said mist tube above said passage, said baffle angling upwardly from adjacent said passage to a gap between said mist tube and said baffle, said mist tube deflecting larger nebulized medicament droplets in the geyser away from said geyser and said passage.

6. An improved aerosol chamber for use with an ultrasonic nebulizer base, as set forth in claim 5, wherein said mist tube passage is a longitudinal slot extending from a lower edge of said mist tube parallel to the axis of said mist tube.

7. An improved aerosol chamber for use with an ultrasonic nebulizer base, as set forth in claim 6, wherein said housing, said mist tube and said baffle are molded as an integral unit from a polycarbonate resin.

* * * * *